(12) United States Patent
Hingston et al.

(10) Patent No.: US 12,285,344 B2
(45) Date of Patent: Apr. 29, 2025

(54) ANTI-MIGRATION STENT

(71) Applicant: BOSTON SCIENTIFIC SCIMED, INC., Maple Grove, MN (US)

(72) Inventors: John A. Hingston, Framingham, MA (US); Michael D. Amos, Ayer, MA (US); Terry V. Brown, Fridley, MN (US); Timothy L. Rubesch, Blaine, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/370,681

(22) Filed: Sep. 20, 2023

(65) Prior Publication Data

US 2024/0009010 A1 Jan. 11, 2024

Related U.S. Application Data

(63) Continuation of application No. 17/411,211, filed on Aug. 25, 2021, now Pat. No. 11,806,258, which is a
(Continued)

(51) Int. Cl.
| | |
|---|---|
| *A61F 2/848* | (2013.01) |
| *A61F 2/04* | (2013.01) |
| *A61F 2/82* | (2013.01) |
| *A61F 2/90* | (2013.01) |
| *A61F 2/91* | (2013.01) |

(52) U.S. Cl.
CPC ............... *A61F 2/848* (2013.01); *A61F 2/82* (2013.01); *A61F 2/90* (2013.01); *A61F 2002/044* (2013.01); *A61F 2002/8486* (2013.01); *A61F 2/91* (2013.01); *A61F 2220/0008* (2013.01);
(Continued)

(58) Field of Classification Search
CPC .... A61F 2/848; A61F 2/82; A61F 2/90; A61F 2002/8486; A61F 2002/044; A61F 2220/0008
See application file for complete search history.

(56) References Cited

U.S. PATENT DOCUMENTS 5,645,559 A * 7/1997 Hachtman ............... D04C 3/48
606/198
6,663,663 B2 12/2003 Kim et al.
(Continued)

FOREIGN PATENT DOCUMENTS

| EP | 2777654 A2 | 9/2014 |
|---|---|---|
| WO | 2011115793 A1 | 9/2011 |

(Continued)

OTHER PUBLICATIONS

International Search Report and Written Opinion, dated May 20, 2016 for International Application No. PCT/US2016/016606.

*Primary Examiner* — Dinah Baria
(74) *Attorney, Agent, or Firm* — Seager, Tufte & Wickhem, LLP

(57) ABSTRACT

An illustrative stent may comprise an elongated tubular member having a first end and a second end and an intermediate region disposed therebetween. The elongated tubular member may include at least one flexible tie affixed to an end thereof. The tie may allow the stent to be attached to a lumen wall with a clip, such as a retention clip, to inhibit migration of the stent within the body lumen.

4 Claims, 9 Drawing Sheets

Related U.S. Application Data continuation of application No. 15/015,812, filed on Feb. 4, 2016, now Pat. No. 11,123,204.

(60) Provisional application No. 62/113,126, filed on Feb. 6, 2015.

(52) U.S. Cl.
CPC . *A61F 2220/0075* (2013.01); *A61F 2230/008* (2013.01)

(56) References Cited

U.S. PATENT DOCUMENTS

| | | | |
|---|---|---|---|
| 7,195,016 B2 | 3/2007 | Loyd et al. | |
| 7,494,461 B2 | 2/2009 | Wells et al. | |
| 7,547,321 B2 | 6/2009 | Silvestri et al. | |
| 7,556,647 B2 | 7/2009 | Drews et al. | |
| 7,879,052 B2 | 2/2011 | Adams et al. | |
| 8,133,240 B2 | 3/2012 | Damarati | |
| 8,187,217 B2 | 5/2012 | Renati et al. | |
| 8,512,414 B2 | 8/2013 | Musani | |
| 8,647,381 B2 | 2/2014 | Essinger et al. | |
| 8,702,785 B2 | 4/2014 | Khan et al. | |
| 8,709,027 B2 | 4/2014 | Adams et al. | |
| 8,715,334 B2 | 5/2014 | Clerc et al. | |
| 8,845,658 B2 | 9/2014 | Adams | |
| 8,974,371 B2 | 3/2015 | Durgin et al. | |
| 2003/0176912 A1 | 9/2003 | Chuter et al. | |
| 2005/0131515 A1 | 6/2005 | Cully et al. | |
| 2006/0253191 A1 | 11/2006 | Salahieh et al. | |
| 2007/0198074 A1 | 8/2007 | Dann et al. | |
| 2009/0254103 A1* | 10/2009 | Deutsch | A61F 2/2481 606/151 |
| 2009/0312603 A1 | 12/2009 | Lam et al. | |
| 2012/0022633 A1 | 1/2012 | Olson et al. | |
| 2012/0053681 A1 | 3/2012 | Alkhatib et al. | |
| 2012/0071987 A1 | 3/2012 | Levy | |
| 2012/0310327 A1 | 12/2012 | Mchugo | |
| 2013/0090714 A1 | 4/2013 | Mchugo | |
| 2013/0172978 A1* | 7/2013 | Vidlund | A61B 17/0401 623/1.12 |
| 2014/0277341 A1 | 9/2014 | Havel et al. | |
| 2014/0277394 A1 | 9/2014 | Roeder et al. | |
| 2014/0277560 A1 | 9/2014 | Walak | |
| 2014/0277573 A1 | 9/2014 | Gill et al. | |
| 2016/0022448 A1 | 1/2016 | Tobis et al. | |
| 2016/0074183 A1 | 3/2016 | Brocker et al. | |
| 2017/0360550 A1* | 12/2017 | Foote | A61F 5/0089 |

FOREIGN PATENT DOCUMENTS

| | | |
|---|---|---|
| WO | 2014081796 A1 | 5/2014 |
| WO | 2014141239 A1 | 9/2014 |

* cited by examiner

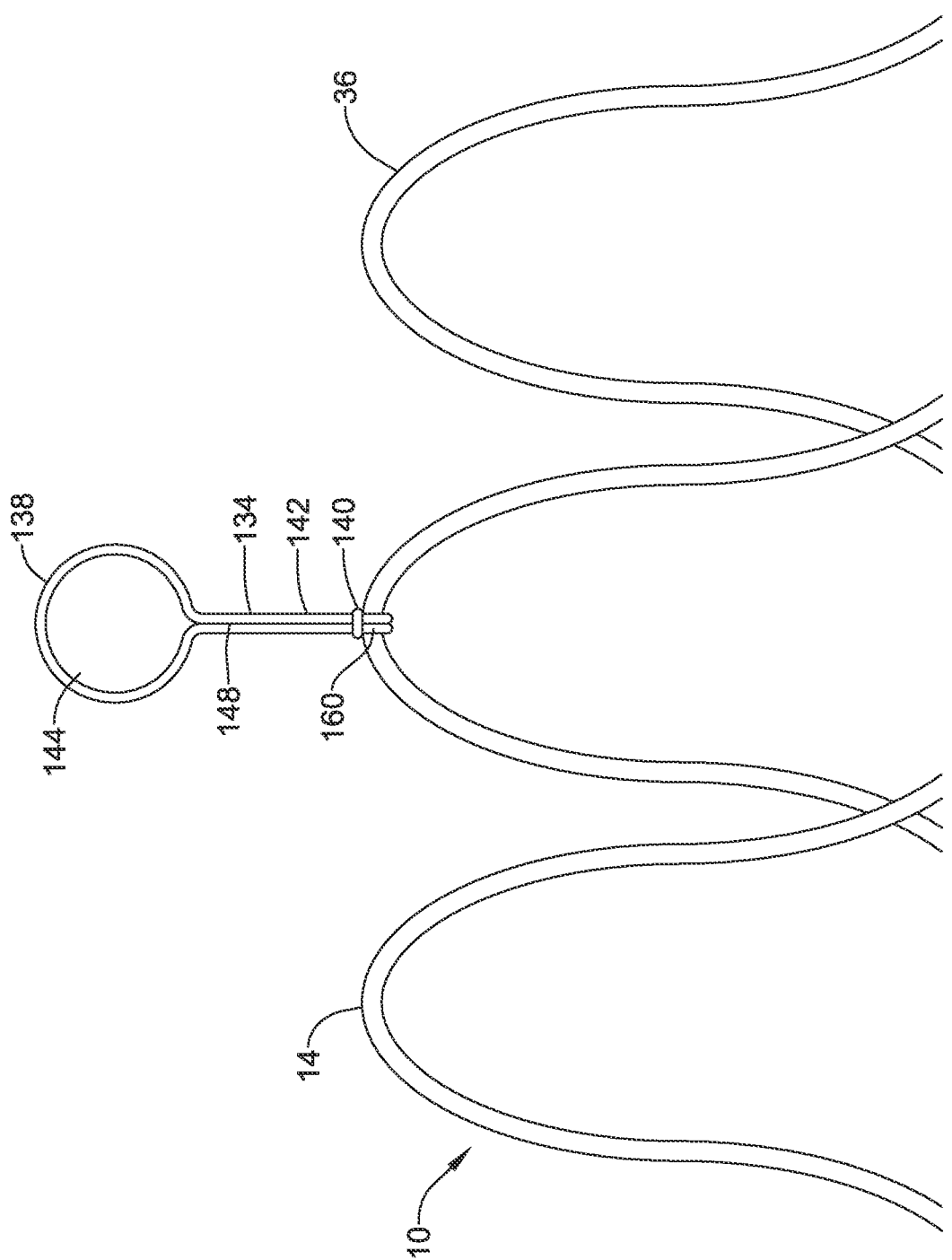

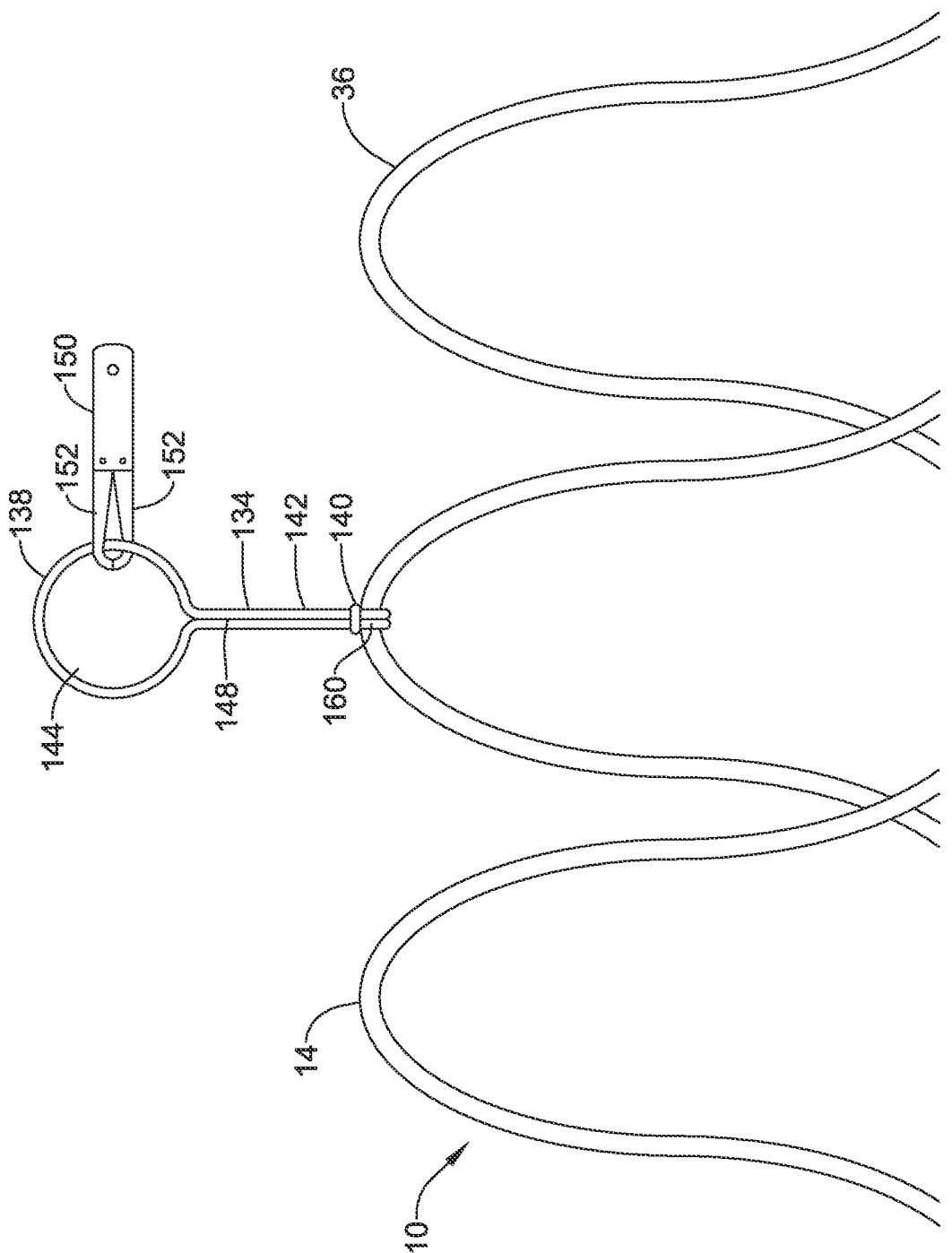

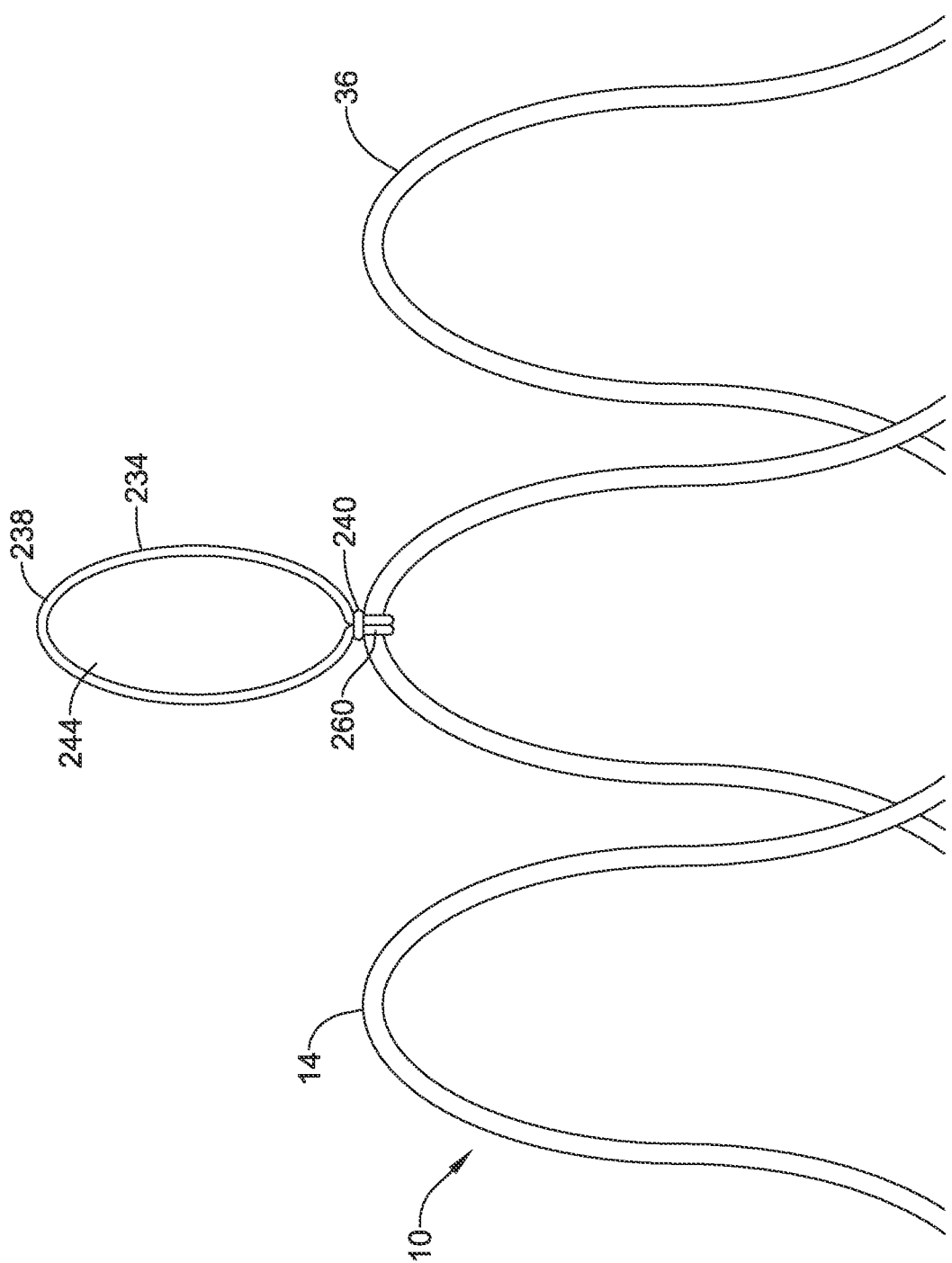

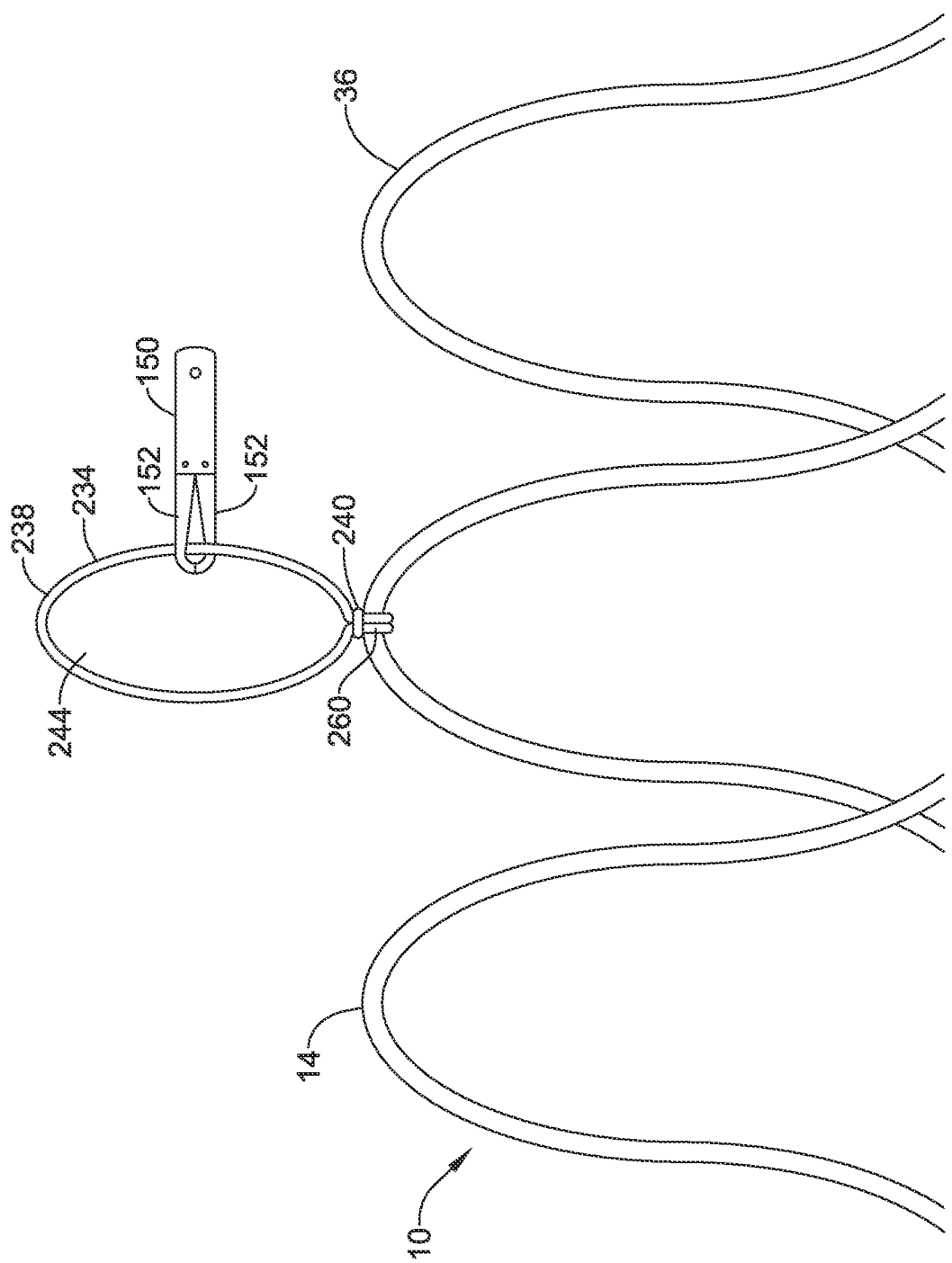

ANTI-MIGRATION STENT

CROSS-REFERENCE TO RELATED APPLICATIONS

This application is a continuation of U.S. application Ser. No. 17/411,211, filed Aug. 25, 2021, which is a continuation of U.S. application Ser. No. 15/015,812, filed Feb. 4, 2016, now U.S. Pat. No. 11,123,204, which claims priority to U.S. Provisional Application No. 62/113,126, filed Feb. 6, 2015, the entire disclosures of which are herein incorporated by reference.

TECHNICAL FIELD

The present disclosure pertains to medical devices, and methods for manufacturing medical devices. More particularly, the present disclosure pertains to an anti-migration stent.

BACKGROUND

Implantable stents are devices that are placed in a body structure, such as a blood vessel or body cavity, to provide support and to maintain the structure open. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices. An example medical device may include a stent. The stent comprises:
an elongated tubular member having a first end, a second end and an intermediate region disposed therebetween, the elongated tubular member comprising at least one filament; and
at least one flexible tie attached to the filament adjacent to the first end of the tubular member, the flexible tie having a first end and a second end.

Alternatively or additionally to any of the embodiments above, the first end of the flexible tie includes a first aperture and the second end of the flexible tie includes a second aperture.

Alternatively or additionally to any of the embodiments above, the stent further comprises an intermediate region disposed between the first aperture and the second aperture of the tie.

Alternatively or additionally to any of the embodiments above, the flexible tie comprises a single loop.

Alternatively or additionally to any of the embodiments above, the flexible tie is knotted to the filament of the tubular member.

Alternatively or additionally to any of the embodiments above, the flexible tie is adhesively secured to the filament of the tubular member.

Alternatively or additionally to any of the embodiments above, the at least one flexible tie comprises two or more flexible ties.

Alternatively or additionally to any of the embodiments above, the at least one flexible tie is biodegradable.

Alternatively or additionally to any of the embodiments above, the stent further comprises at least one clip configured to be secured to the at least one flexible tie.

Alternatively or additionally to any of the embodiments above, the clip comprises a pair of jaws configured to clamp around the at least one flexible tie.

An example kit for securing a stent comprises:
a stent having a first end, a second end and an intermediate region disposed therebetween;
at least one flexible tie; and
at least one clip.

Alternatively or additionally to any of the embodiments above, the flexible tie comprises a single loop.

Alternatively or additionally to any of the embodiments above, a first portion of the single loop is secured to a second portion of the single loop to define a first aperture and a second aperture.

Alternatively or additionally to any of the embodiments above, the clip comprises a pair of jaws.

Alternatively or additionally to any of the embodiments above, the clip comprises a hemostasis clip, such as, but not limited to the Resolution® Clip made by Boston Scientific, Corporation.

Alternatively or additionally to any of the embodiments above, wherein the flexible tie is secured to the stent adjacent to the first end of the stent.

Another example system for reducing migration of a stent comprises:
an elongated tubular member having a first end, a second end and an intermediate region disposed therebetween, the elongated tubular member comprising at least one woven filament;
a retainer; and
at least one tie extending between the elongated tubular member and the retainer.

Alternatively or additionally to any of the embodiments above, the retainer comprises at least one aperture for receiving the at least one tie.

Alternatively or additionally to any of the embodiments above, the at least one tie comprises a distal end including a clip, the clip configured to secure the tie to the tubular member.

Alternatively or additionally to any of the embodiments above, the clip comprise a pair of jaws configured to clasp the tubular member.

Alternatively or additionally to any of the embodiments above, the retainer comprises a "U"-shape.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which:
FIG. 2B is a close up view of an end portion of an illustrative anti-migration stent.

FIG. 2C a close up view of an end portion of the illustrative anti-migration stent of FIG. 2B including a fixation mechanism, such as a hemostasis clip device.

FIG. 3A is a close up view of an end portion of another illustrative anti-migration stent.

FIG. 3B a close up view of an end portion of the illustrative anti-migration stent of FIG. 3A including a fixation mechanism.

Figure 1:
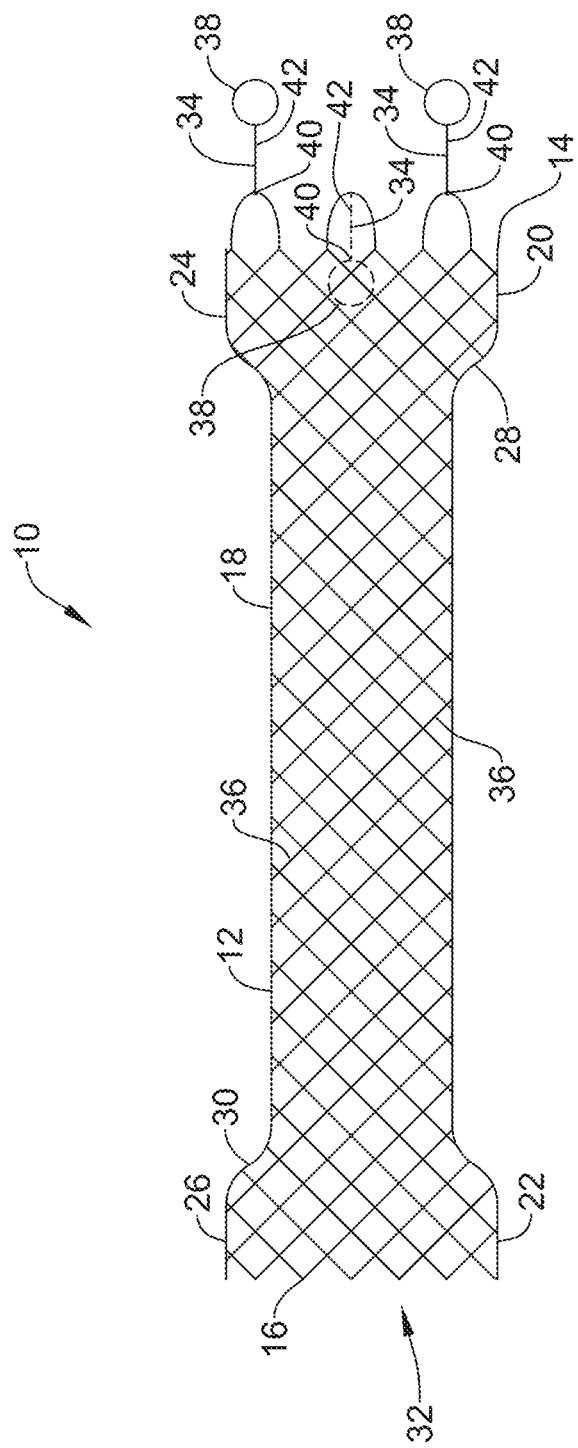
FIG. 1 is a side view of an illustrative anti-migration stent.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In some instances, it may be desirable to provide an endoluminal implant, or stent, that can deliver luminal patency in patients with esophageal strictures. Such stents may be used in patients experiencing dysphagia, sometimes due to esophageal cancer. An esophageal stent may allow a patient to maintain nutrition via oral intake during cancer treatment or palliation periods. However, a common complication of gastrointestinal (GI) stents is stent migration. It may be desirable to provide a stent that can deliver luminal patency while minimizing migration of the stent. While the embodiments disclosed herein are discussed with reference to esophageal stents, it is contemplated that the stents described herein may be used and sized for use in other locations such as, but not limited to: bodily tissue, bodily organs, vascular lumens, non-vascular lumens and combinations thereof, such as, but not limited to, in the coronary or peripheral vasculature, trachea, bronchi, colon, small intestine, biliary tract, urinary tract, prostate, brain, stomach and the like.

FIG. 1 illustrates a side view of an illustrative endoluminal implant 10, such as, but not limited to, a stent. In some instances, the stent 10 may be formed from an elongated tubular member 12. While the stent 10 is described as generally tubular, it is contemplated that the stent 10 may take any cross-sectional shape desired. The stent 10 may have a first, or proximal, end 14, a second, or distal, end 16, and an intermediate region 18 disposed between the first end 14 and the second end 16. The stent 10 may include a lumen 32 extending from a first opening adjacent the first end 14 to a second opening adjacent to the second end 16 to allow for the passage of food, fluids, etc.

The stent 10 may be expandable from a first collapsed configuration (not explicitly shown) to a second expanded configuration. The stent 10 may be structured to extend across a stricture and to apply a radially outward pressure to the stricture in a lumen to open the lumen and allow for the passage of foods, fluids, air, etc.

The stent 10 may have a woven structure, fabricated from a number of filaments or struts 36. In some embodiments, the stent 10 may be braided with one filament. In other embodiments, the stent 10 may be braided with several filaments, as is found, for example, in the WallFlex®, WALLSTENT®, and Polyflex® stents, made and distributed by Boston Scientific, Corporation. In another embodiment, the stent 10 may be knitted, such as the Ultraflex™ stents made by Boston Scientific, Corporation. In yet another embodiment, the stent 10 may be of a knotted type, such the Precision Colonic™ stents made by Boston Scientific, Corporation. In still another embodiment, the stent 10 may be a laser cut tubular member, such as the EPIC™ stents made by Boston Scientific, Corporation. A laser cut tubular member may have an open and/or closed cell geometry including one or more interconnected filaments. In some instances, an inner and/or outer surface of the stent 10 may be entirely, substantially or partially, covered with a polymeric covering or coating. For example, a covering or coating which may help reduce food impaction and/or tumor or tissue ingrowth.

In some instances, in the expanded configuration, the stent 10 may include a first end region 20 and a second end region 22. In some embodiments, the first end region 20 and the second end region 22 may include retention features or anti-migration flared regions 24, 26 positioned adjacent to the first end 14 and the second end 16 of the stent 10. The anti-migration flared regions 24, 26 may be configured to engage an interior portion the walls of the esophagus. In some embodiments, the retention features, or flared regions 24, 26 may have a larger diameter than an intermediate region 18 of the stent 10 to prevent the stent 10 from migrating once placed in the esophagus. It is contemplated that the transition 28, 30 from the cross-sectional area of the intermediate region 18 to the retention features or flared regions 24, 26 may be gradual, sloped, or occur in an abrupt step-wise manner, as desired.

In some embodiments, the first anti-migration flared region 24 may have a first outer diameter and the second anti-migration flared region 26 may have a second outer diameter. In some instances, the first and second outer diameters may be approximately the same, while in other instances, the first and second outer diameters may be different. In some embodiments, the stent 10 may include only one or none of the anti-migration flared regions 24, 26. For example, the first end region 20 may include an anti-migration flare 24 while the second end region 22 may have an outer diameter similar to the intermediate region 18. It is further contemplated that the second end region 22 may include an anti-migration flare 26 while the first end region 20 may have an outer diameter similar to an outer diameter of the intermediate region 18. In some embodiments, the stent 10 may have a uniform outer diameter from the first end 14 to the second end 16. In some embodiments, the outer diameter of the intermediate region 18 may be in the range of 15 to 25 millimeters. The outer diameter of the anti-migration flares 24, 26 may be in the range of 20 to 30 millimeters. It is contemplated that the outer diameter of the stent 10 may be varied to suit the desired application.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, nitinol and Elgiloy®. Depending the on material selected for construction, the stent 10 may be self-expanding or require an external force to expand the stent 10. In some embodiments, fibers may be used to make the stent 10, which may be cored fibers, for example, having an outer shell made of nitinol having a platinum core. It is further contemplated the stent 10 may be formed from polymers including, but not limited to, polyethylene terephthalate (PET).

The stent 10 may further include one or more ties (e.g., sutures or tethers 34) attached adjacent to the first end 14 of the stent 10. As will be discussed in more detail below, the ties 34 may allow a physician to attach one or more fixation mechanisms or retention clips simultaneously to the ties 34 and the body lumen. In some instances, the fixation mechanism may be a hemostasis clip, such as, but not limited to the Resolution® Clip made by Boston Scientific, Corporation, While the fixation mechanism is described as a clip, it is contemplated that any structure that allows for attachment of the tie 34 to the lumen wall may be used to secure the tie 34 within the lumen. It is contemplated that the one or more ties 34 may be attached to the stent 10 at any point along the length thereof. For example, in some embodiments, the ties 34 may be affixed adjacent to the intermediate region 18 while in other instances, the ties 34 may be affixed adjacent to the second end 16. This may allow the stent 10 to be anchored such that proximal, distal, or both proximal and distal movement is prevented. In some embodiments, the ties 34 may be provided in a kit including the stent 10 and clips. In some instances, the stent 10 may be delivered with the ties 34 previously attached thereto. This may allow a physician to attach the desired number of ties 34 to the stent 10 prior to use. A kit may also include a stent 10 with attached ties 34 and one or more clips. While the stent 10 is shown as having two ties 34, it is contemplated that the stent 10 may include any number of ties 34 desired, such as, but not limited to, one, two, three, four, or more. The ties 34 may be made of a flexible, bendable material. In some instances, the ties 34 may be formed from suture material, or other biocompatible material. It is contemplated that the ties 34 may be formed from a biodegradable material that may "fall away" or be absorbed by the patient's body after a period of time, such as two to three weeks after the stent 10 is placed.

The ties 34 may include a first end 38, a second end 40, and an intermediate region 42 disposed therebetween. The first end 38 may include a loop or other structure that allows a clamp, clip or other retention mechanism to grasp a portion of the tie. In some embodiments, the first end 38 may be a solid or substantially solid enlarged portion that provides a surface area for the clip to grasp. In other embodiments, the first end 38 may have a substantially "T" shape that provides a region for the clip to grasp. The second end 40 of the tie 34 may be affixed to a filament/strut 36 of the stent 10. It is contemplated that the second end 40 may be affixed or attached to the stent 10 in a number of suitable ways. For example, the tie 34 may be adhesively secured to the stent 10 or the tie 34 may be knotted, looped, or wound about a filament 36. The intermediate region 42 of the tie 34 may be any length desired to provide a physician with easy access to attach a clip to the first end 38 of the tie 34. While the ties 34 are illustrated as having a similar length, it is contemplated that the ties 34 may have differing lengths to allow for staggering of the clips, if desired.

The second end 40 of the tie 34 may be secured to the stent 10 such that the tie 34 extends beyond or is capable of extending beyond the tubular portion 12 of the stent 10. For example, as shown in FIG. 1, the tie 34 may be secured adjacent to the proximal end 14 of the stent 10 and extend proximally therefrom. While not explicitly shown, it is contemplated that the tie 34 may be secured adjacent to the distal end 15 of the stent 10 and extend distally therefrom. When a clip is used to secure the stent 10 within a lumen, the tie 34 may be moved away from the tubular portion 12 of the stent 10 to allow the physician to easily secure a portion of the tissue and the tie 34 within the securing mechanism. As will be described in more detail below, if a physician chooses not to use one or more of the ties 34, the tie(s) 34 may be allowed to hang from the stent 10. In some instances, gravity may draw the ties(s) 34 into the lumen 32 of the stent 10 when they are not secured with a retention mechanism or clip.

Figure 5:
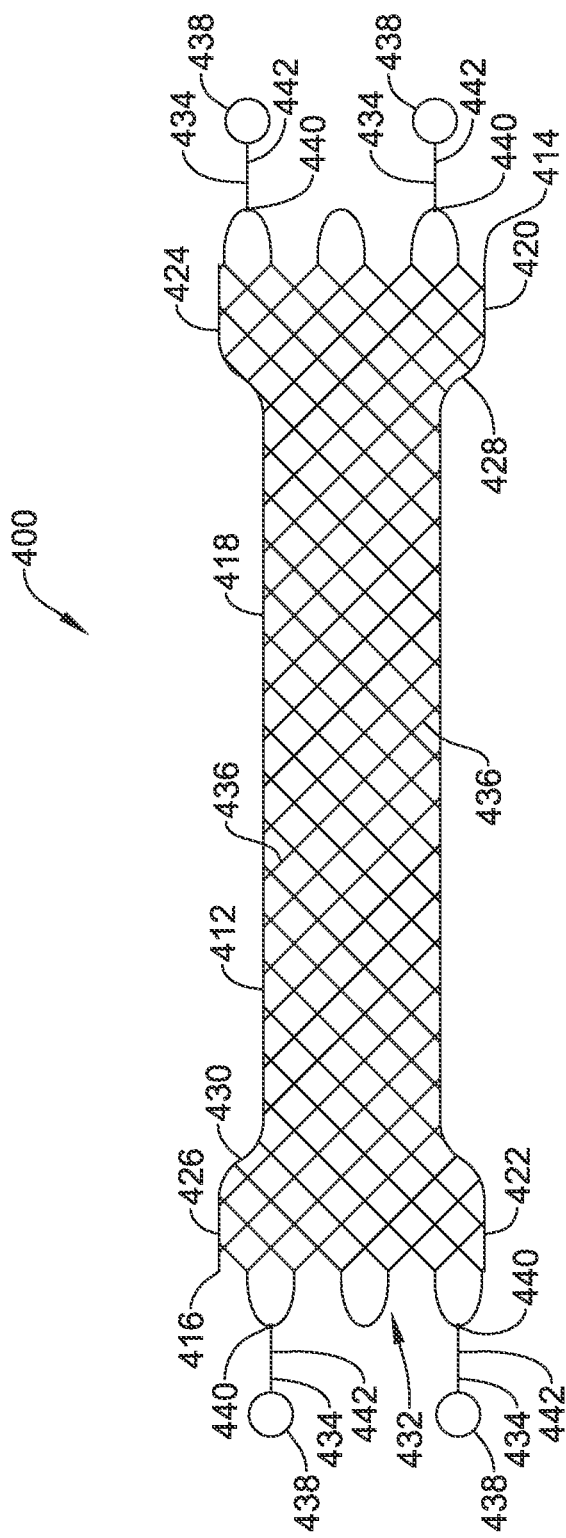
FIG. 5 is a side view of another illustrative anti-migration stent.

Referring additionally to FIG. 5, which illustrates a side view of another illustrative endoluminal implant 400, such as, but not limited to, a stent. The stent 400 may be similar in form and function to the stent 10 described above. In some instances, the stent 400 may be formed from an elongated tubular member 412. While the stent 400 is described as generally tubular, it is contemplated that the stent 400 may take any cross-sectional shape desired. The stent 400 may have a first end 414, such as a proximal end, a second end 416, such as a distal end, and an intermediate region 418 disposed between the first end 414 and the second end 416. The stent 400 may include a lumen 432 extending from a first opening adjacent the first end 414 to a second opening adjacent to the second end 416 to allow for the passage of food, fluids, etc.

The stent 400 may be expandable from a first collapsed configuration (not explicitly shown) to a second expanded configuration. The stent 400 may be structured to extend across a stricture and to apply a radially outward pressure to the stricture in a lumen to open the lumen and allow for the passage of foods, fluids, air, etc.

In some embodiments, the stent 400 may have a woven structure, fabricated from a number of filaments or struts 436. In another embodiment, the stent 400 may be a laser cut tubular member. In some instances, an inner and/or outer surface of the stent 400 may be entirely, substantially or partially, covered with a polymeric covering or coating. For example, a covering or coating which may help reduce food impaction and/or tumor or tissue ingrowth.

In some instances, in the expanded configuration, the stent 400 may include a first end region 420 and a second end region 422. In some embodiments, the first end region 420 and the second end region 422 may include retention features or anti-migration flared regions 424, 426 positioned adjacent to the first end 414 and the second end 416 of the stent 400. The anti-migration flared regions 424, 426 may be configured to engage an interior portion the walls of the body lumen, such as the esophagus. In some embodiments, the retention features, or flared regions 424, 426 may have a larger diameter than an intermediate region 418 of the stent 400 to prevent the stent 400 from migrating once placed in the body lumen, such as the esophagus. It is contemplated that the transition 428, 430 from the cross-sectional area of the intermediate region 418 to the retention features or flared regions 424, 426 may be gradual, sloped, or occur in an abrupt step-wise manner, as desired.

In some embodiments, the first anti-migration flared region 424 may have a first outer diameter and the second anti-migration flared region 426 may have a second outer diameter. In some instances, the first and second outer diameters may be approximately the same, while in other instances, the first and second outer diameters may be different. In some embodiments, the stent 400 may include only one or none of the anti-migration flared regions 424, 426. In some embodiments, the stent 400 may have a uniform outer diameter from the first end 414 to the second end 416. In some embodiments, the outer diameter of the intermediate region 418 may be in the range of 15 to 25 millimeters. The outer diameter of the anti-migration flares 424, 426 may be in the range of 20 to 30 millimeters. It is contemplated that the outer diameter of the stent 400 may be varied to suit the desired application.

It is contemplated that the stent 400 can be made from a number of different materials such as, but not limited to, metals, metal alloys, shape memory alloys and/or polymers, as desired, enabling the stent 400 to be expanded into shape when accurately positioned within the body. In some instances, the material may be selected to enable the stent 400 to be removed with relative ease as well. For example, the stent 400 can be formed from alloys such as, but not limited to, nitinol and Elgiloy®. Depending the on material selected for construction, the stent 400 may be self-expanding or require an external force to expand the stent 400. In some embodiments, fibers may be used to make the stent 400, which may be cored fibers, for example, having an outer shell made of nitinol having a platinum core. It is further contemplated the stent 400 may be formed from polymers including, but not limited to, polyethylene terephthalate (PET).

The stent 400 may further include one or more ties (e.g., sutures or tethers 434) attached to the tubular member 412, such as adjacent to the first end 414 of the stent 400. As will be discussed in more detail below, the ties 434 may allow a physician to attach one or more fixation mechanisms or clips simultaneously to the ties 434 and the body lumen. In some instances, the fixation mechanism may be a hemostasis clip, such as, but not limited to the Resolution® Clip made by Boston Scientific, Corporation, While the fixation mechanism is described as a clip, it is contemplated that any structure that allows for attachment of the tie 434 to the lumen wall may be used to secure the tie 434 within the lumen. While the illustrative embodiment illustrates ties 434 attached to both the first and second ends 414, 416, it is contemplated that the one or more ties 434 may be attached to the stent 400 at any point along the length thereof. For example, in some embodiments, the ties 434 may be affixed adjacent to the intermediate region 418 while in other instances, the ties 434 may be affixed adjacent to either the first end 414 or the second end 416, but not both. This may allow the stent 400 to be anchored such that proximal, distal, or both proximal and distal movement is prevented. In some embodiments, the ties 434 may be provided in a kit including the stent 400 and clips. In some instances, the stent 400 may be delivered with the ties 434 previously attached thereto. This may allow a physician to attach the desired number of ties 434 to the stent 400 prior to use. A kit may also include a stent 400 with attached ties 434 and one or more clips. While the stent 400 is shown as having four ties 434, it is contemplated that the stent 400 may include any number of ties 434 desired, such as, but not limited to, one, two, three, four, or more. The ties 434 may be made of a flexible, bendable material. In some instances, the ties 434 may be formed from suture material, or other biocompatible material. It is contemplated that the ties 434 may be formed from a biodegradable material that may "fall away" or be absorbed by the patient's body after a period of time, such as two to three weeks after the stent 400 is placed.

The ties 434 may include a first end 438, a second end 440, and an intermediate region 442 disposed therebetween. The first end 438 may include a loop or other structure that allows a clamp, clip or other retention mechanism to grasp a portion of the tie. In some embodiments, the first end 438 may be a solid or substantially solid enlarged portion that provides a surface area for the clip to grasp. In other embodiments, the first end 438 may have a substantially "T" shape that provides a region for the clip to grasp. The second end 440 of the tie 434 may be affixed to a filament/strut 436 of the stent 400. It is contemplated that the second end 40 may be affixed or attached to the stent 400 in a number of suitable ways. For example, the tie 434 may be adhesively secured to the stent 400 or the tie 434 may be knotted, looped, or wound about a filament 436. The intermediate region 442 of the tie 434 may be any length desired to provide a physician with easy access to attach a clip to the first end 438 of the tie 434. While the ties 434 are illustrated as having a similar length, it is contemplated that the ties 434 may have differing lengths to allow for staggering of the clips, if desired.

The second end 440 of the tie 434 may be secured to the stent 400 such that the tie 434 extends beyond or is capable of extending beyond the tubular portion 412 of the stent 400. For example, as shown in FIG. 5, one or more ties 434 may be secured adjacent to the proximal end 414 of the stent 400 and extend proximally therefrom and one or more ties 434 may be secured adjacent to the distal end 416 of the stent and extend distally therefrom. When a clip is used to secure the stent 400 within a lumen, the tie 434 may be moved away from the tubular portion 412 of the stent 400 to allow the physician to easily secure a portion of the tissue and the tie 434 within the securing mechanism. As will be described in more detail below, if a physician chooses not to use one or more of the ties 434, the tie(s) 434 may be allowed to hang from the stent 400. In some instances, gravity may draw the ties(s) 434 into the lumen 432 of the stent 400 when they are not secured with a retention mechanism or clip.

Figure 2A:
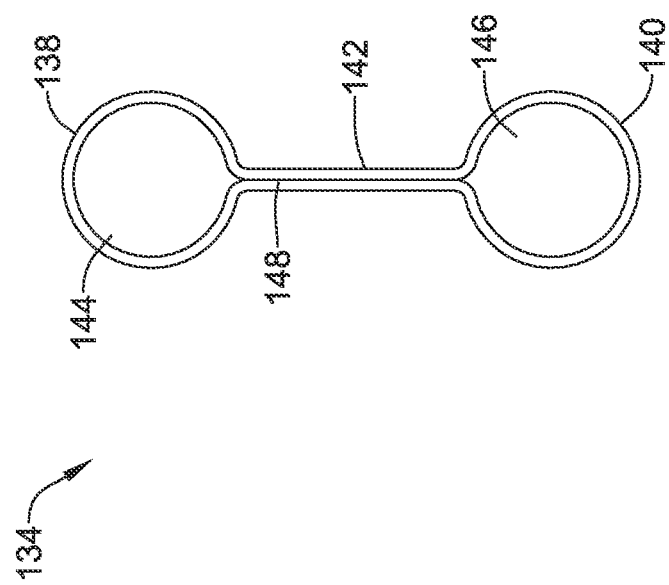
FIG. 2A is a side view of an illustrative tie.

Referring now to FIG. 2A, which illustrates a close up view of an illustrative tie 134, the tie 134 may include a first looped end 138 having a first opening or aperture 144 and a second looped end 140 having a second opening or aperture 146. The first looped end 138 and the second looped end 140 may be connected by an intermediate region 142. In some instances, the tie 134 may be formed as a unitary structure. For example, the tie 134 may be formed as a single loop with portions of the loop 148 secured together along the intermediate region 142 to form the first opening 144 and the second opening 146. In other instances, the tie 134 may be formed of separate components secured to one another. For example, one or more of the first looped end 138, second looped end 140, and/or the intermediate region 142 may be formed as an individual component and secured to the remaining components, as desired. In yet another embodiment, the tie 134 may be formed as a generally solid rectangular or oblong structure. One or more slits may be made in the rectangular structure adjacent to the first end and the second end thereof to form the first opening 144 and the second opening 146. It is contemplated that the tie 134 may be formed in any manner that allows it to be secured to a stent, such as stent 10, and to a clip. In some embodiments, the tie 134 may be provided with a clip, clamp, or other mechanism configured to grasp or surround a portion of the stent 10.

FIG. 2B is a close up side view of an illustrative stent 10 with a tie 134 secured adjacent to the first end 14 of the stent 10. The tie 134 may be looped around a filament 36 of the stent 10 to secure the tie 134 to the stent 10. For example, the tie 134 may be placed on a first side (for example, an inner or outer surface) of the filament 36. The first looped end 138 may be wound or wrapped around the filament 36 on the second side. The first looped end 138 may be pushed through the second opening 146 and pulled to form a knot 160 and secure the tie 134 to the stent 10 in a looped manner, as illustrated in FIG. 2B. In some instances, an adhesive may be used in addition to, or in place of, the knot 160.

FIG. 2C is a close up side view of an illustrative stent 10 with a tie 134 secured adjacent to the first end 14 of the stent 10 and an illustrative clip 150 affixed to the tie 134. The stent 10 may be delivered and deployed to the target location using a stent delivery system and/or an endoscope, gastroscope or other guide means (not explicitly shown). The stent 10 may be advanced to the target location in a collapsed configuration and then expanded into an enlarged configuration. In some instances, it may be desirable to attach the stent 10 to the lumen to reduce or prevent migration of the stent 10. When a 150 clip is used to secure the stent 10 within a lumen, the tie 134 may be moved away from the tubular portion 12 of the stent 10 to allow the physician to easily secure a portion of the tissue and the tie 134 within the securing mechanism. For example, the tie 134 may extend proximally from the proximal end 14 of the stent 10 and be secured to the body lumen proximal of the proximal end 14 of the stent. In an esophageal application, this may reduce distal migration or movement of the stent 10. This is just an example. In other applications, it may be desirable to secure a tie 134 distal of the distal end of the stent 10 to prevent proximal migration, for example. The physician may use a clip 150 to grip both a portion of the tie 134 (e.g., the first looped end 138 of the tie 134) and tissue of the lumen thus securing the stent 10 within the lumen. If a physician chooses not to use one or more of the ties 134, the tie 134 may hang, or be otherwise disposed, within the lumen 32 of the stent 10. The physician may choose to use as many clips 150 and/or ties 134 as they feel necessary to prevent migration of the stent 10. In some instances, more than one clip 150 may be used with a single tie 134. The clip 150 may include a pair of jaws 152 that may be opened and closed to grasp the tie 134 and tissue therebetween. In some instances, the jaws 152 may be able to open and close a number of times prior to deploying the clip 150 to aid in positioning and/or repositioning of the clip 150. While not explicitly shown, the clip 150 may include a delivery system configured to advance the clip 150, open and close the jaws 152, and deploy the clip 150 within the lumen. The clip 150 may be left in place with the stent 10 or may be removed after a period of time. For example, the clip(s) 150 may be removed after tissue ingrowth has secured the stent 10 in place.

FIG. 3A is a close up side view of an illustrative stent 10 with another illustrative tie 234 secured adjacent to the first end 14 of the stent 10. The tie 234 may be formed of a single loop of material, similar to a rubber band, defining an opening 244. The tie 234 may be looped around a filament 36 of the stent 10 to secure the tie 234 to the stent 10. For example, the tie 234 may be placed on a first side (for example, an inner or outer surface) of the filament 36. A first end 238 may be wound or wrapped around the filament 36 on the second side. The first end 238 may be pushed through the opening 246 adjacent to the second end 240 and pulled to form a knot 260 and secure the tie 234 to the stent 10 in a looped manner, as illustrated in FIG. 3A. In some instances, an adhesive may be used in addition to, or in place of, the knot 260.

FIG. 3B is a close up side view of an illustrative stent 10 with a tie 234 secured adjacent to the first end 14 of the stent 10 and an illustrative clip 250 affixed to the tie 234. The stent 10 may be delivered and deployed to the target location using a stent delivery system and/or an endoscope, gastroscope or other guide means (not explicitly shown). The stent 10 may be advanced to the target location in a collapsed configuration and then expanded into an enlarged configuration. In some instances, it may be desirable to attach the stent 10 to the lumen to reduce or prevent migration of the stent 10. The physician may use a clip 150 to grip both the tie 134 and tissue of the lumen thus securing the stent 10 within the lumen. If a physician chooses not to use one or more of the ties 234, the tie 234 may hang, or be otherwise disposed, within the lumen 32 of the stent 10. The physician may choose to use as many clips 150 and/or ties 234 as they feel necessary to prevent migration of the stent 10. In some instances, more than one clip 150 may be used with a single tie 234. The clip 150 may include a pair of jaws 152 that may be opened and closed to grasp the tie 234 and tissue therebetween. In some instances, the jaws 152 may be able to open and close a number of times prior to deploying the clip 150 to aid in positioning and/or repositioning of the clip 150. While not explicitly shown, the clip 150 may include a delivery system configured to advance the clip 150, open and close the jaws 152, and deploy the clip 150 within the lumen.

Figure 4A:
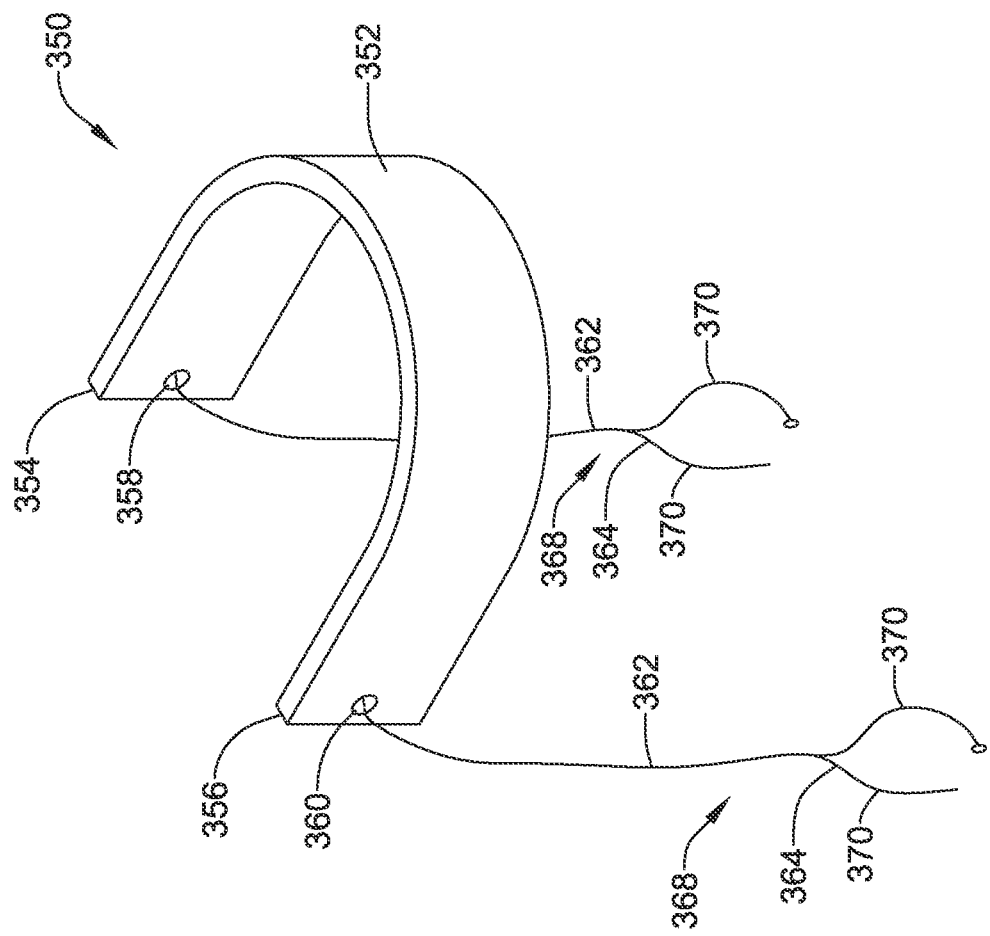
FIG. 4A is a perspective view of another illustrative stent fixation mechanism.
Figure 4B:
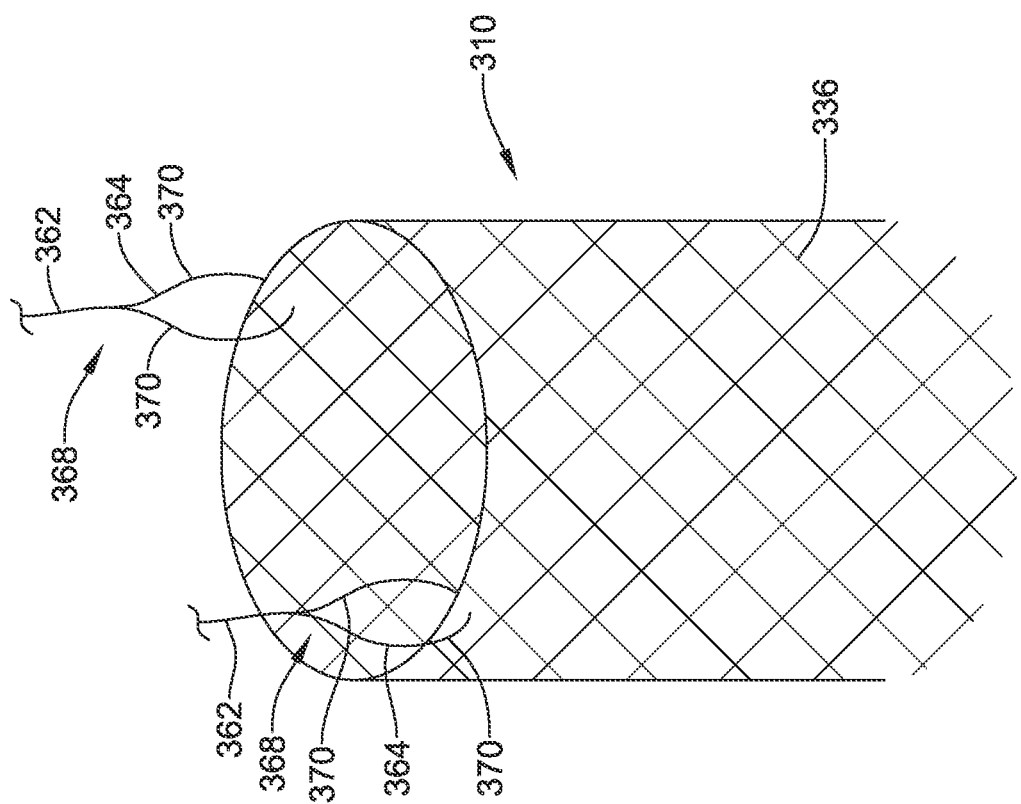
FIG. 4B is a perspective view of the illustrative stent fixation mechanism of FIG. 4A and an illustrative stent.

FIGS. 4A and 4B illustrate another illustrative system 350 for reducing and/or preventing migration of an esophageal stent, such as stent 310. The stent 310 may be similar in form and function to the stent 10 described above. The system 350 may be a mandible system configured to be placed in a patient's mouth. The system 350 may include a retainer 352 sized and shaped to be positioned over a patient's bottom teeth. The retainer 352 may be generally "U"-shaped having a first leg 354 and a second leg 356. The first and second legs 354, 356 may each include an aperture 358, 360 extending therethrough. Alternatively, only one of the legs 354, 356 may include an aperture 358, 360. In some instances, the apertures may be positioned such along the retainer 352 such that they are near the back of a patient's mouth when the retainer is in a patient's mouth. One or more tethers or ties 362 may be attached to the apertures 358, 360. The ties 362 may be knotted, wound, wrapped, adhesively secured, or otherwise secured to the retainer 352. The ties 362 may be made of a flexible, bendable material. In some instances, the ties 362 may be formed from suture material, or other biocompatible material. It is contemplated that the ties 362 may be formed from a biodegradable material that may "fall away" or be absorbed by the patient's body after a period of time, such as two to three weeks after a stent is placed. Each of the ties 362 may include a clamp or clip 364 disposed adjacent a distal end 368 thereof. The clip 364 may include a pair of jaws 370 capable of opening and closing. In some instances the clip 364 may include a spring to bias the jaws 370 toward a closed position to grip tissue, etc. therebetween. The jaws 370 may clasp around a portion of a stent 310, such as a filament 336, to secure the tie 362 to the stent 310. Alternatively, the tie 362 may be tied to, knotted around or adhesively secured to the stent 310. It is contemplated that the retainer 352 may be removed from a patient's mouth after a period of time, such as but not limited, one week, or until the stent 310 is set in place on its own. The ties 362 may be disconnected (for example, untied, cut, etc.) and allowed to drop or hang from the stent 310.

The stents, delivery systems, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. In some other embodiments, a superelastic alloy, for example a superelastic nitinol can be used to achieve desired properties.

In at least some embodiments, portions or all of the stents or delivery systems may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents or delivery systems in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents or delivery systems to achieve the same result.

In some embodiments, a degree of Magnetic Resonance Imaging (MM) compatibility is imparted into the stents or delivery systems. For example, the stents or delivery systems or portions thereof, may be made of a material that does not substantially distort the image and create substantial artifacts (i.e., gaps in the image). Certain ferromagnetic materials, for example, may not be suitable because they may create artifacts in an MRI image. The stents or delivery systems or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for the stents or delivery systems may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for delivering a stent to a lumen, the method comprising:
    advancing a stent to a target location in a collapsed configuration, the stent comprising:
        an elongated tubular member having a first end, a second end and an intermediate region disposed therebetween, the elongated tubular member comprising at least one filament; and
    a flexible tie having a distal end attached to the filament adjacent to the first end of the elongated tubular member and extending proximally therefrom;
    expanding the stent into an enlarged configuration; and
    positioning a retainer in a mouth of a patient, a proximal end of the flexible tie attached to a portion of the retainer.

2. The method of claim 1, wherein the retainer comprises at least one aperture for receiving the flexible tie.

3. The method of claim 1, wherein the distal end of the flexible tie includes a clip, the clip configured to secure the flexible tie to the elongated tubular member.

4. The method of claim 3, wherein the clip comprises a pair of jaws configured to clasp the elongated tubular member.

* * * * *